(12) United States Patent
Thai

(10) Patent No.: US 9,949,727 B2
(45) Date of Patent: *Apr. 24, 2018

(54) ANTI-ROTATION INSTRUMENT

(71) Applicant: Hung M. Thai, San Jose, CA (US)

(72) Inventor: Hung M. Thai, San Jose, CA (US)

(*) Notice: Subject to any disclaimer, the term of this patent is extended or adjusted under 35 U.S.C. 154(b) by 908 days.

This patent is subject to a terminal disclaimer.

(21) Appl. No.: 14/167,081

(22) Filed: Jan. 29, 2014

(65) Prior Publication Data

US 2014/0147805 A1    May 29, 2014

Related U.S. Application Data

(63) Continuation-in-part of application No. 13/604,369, filed on Sep. 5, 2012, now Pat. No. 8,690,571.

(51) Int. Cl.
| | |
|---|---|
| *A61C 3/00* | (2006.01) |
| *A61B 17/00* | (2006.01) |
| *A61B 1/247* | (2006.01) |

(52) U.S. Cl.
CPC ............. *A61B 17/00* (2013.01); *A61B 1/247* (2013.01); *A61C 3/00* (2013.01)

(58) Field of Classification Search
CPC ......... A61C 3/00; A61M 1/0086; A61M 5/00; A61M 5/34; A61M 39/10; A61M 39/14; A61M 16/0816; A61M 25/0097; A61M 39/00; A61M 2039/087; A61M 2039/1033; A61M 2039/1038; A61M 2039/1061; A61M 2039/1066; A61M 39/20; A61B 17/00; A61B 1/247

USPC ... 433/72, 127, 166, 75, 141–147, 172–176; 29/2.25, 417, 557, 558; 76/101.1, 106, 76/119

See application file for complete search history.

(56) References Cited

U.S. PATENT DOCUMENTS

| | | | | |
|---|---|---|---|---|
| 631,732 | A | 8/1899 | Ivory | |
| 634,732 | A * | 10/1899 | Ivory | ........................ B25G 1/00 |
| | | | | 279/99 |
| 2,604,693 | A | 7/1952 | Schierstead | |
| 3,376,644 | A | 4/1968 | Clark | |
| 4,251,214 | A * | 2/1981 | Schnall | ................... A61O 5/025 |
| | | | | 30/329 |
| 4,677,985 | A * | 7/1987 | Bro | ......................... A61B 5/031 |
| | | | | 600/504 |
| 5,246,370 | A * | 9/1993 | Coatoam | .................. A61C 8/00 |
| | | | | 433/173 |

(Continued)

*Primary Examiner* — Cris L Rodriguez
*Assistant Examiner* — Mirayda A Aponte

(57) ABSTRACT

The present invention features an anti-rotation instrument system which could be used in all health professions including medical, dental, and any other specialties. The system includes an anti-rotation instrument device featuring a main handle, a first removable hand grip and a first instrumental tip. The first removable hand grip is attached to a first female screw cavity located on the main handle. One end of the instrumental tips passes through a channel located within first hand grip with an anti-rotation key located on the instrumental tip securely residing within a dent located on a distal end of the first removable hand grip having threading located on an end of the instrumental tip that is subsequently screwed into a first female screw cavity of the main handle such that the first hand grip is tightly sandwiched between the first instrumental tip and main body.

9 Claims, 5 Drawing Sheets

(56) References Cited

U.S. PATENT DOCUMENTS

| | | | |
|---|---|---|---|
| 6,109,918 A * | 8/2000 | Hammond | A61C 3/00 433/141 |
| 6,997,709 B2 | 2/2006 | Kangasniemi et al. | |
| 8,690,571 B2 * | 4/2014 | Thai | A61C 3/00 433/147 |
| 2004/0115588 A1 | 6/2004 | Sommers et al. | |
| 2007/0027443 A1 | 2/2007 | Rose et al. | |
| 2007/0031788 A1 * | 2/2007 | Chao | A61C 3/00 433/144 |
| 2008/0124674 A1 | 5/2008 | Meuchel | |
| 2011/0223559 A1 * | 9/2011 | Jamnia | A61C 3/00 433/143 |

\* cited by examiner

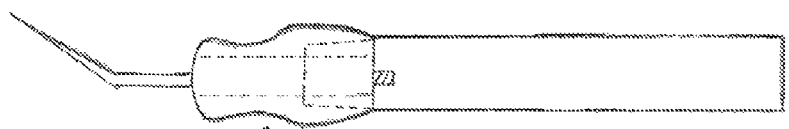
FIG. 13
EASY GRIPPED DESIGN
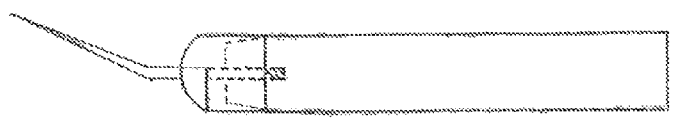
FIG. 14: ANTI-ROTATION HANDLE WITH ANTI-ROTATION TIP
FIG. 15: ANTI-ROTATION TIP

ANTI-ROTATION INSTRUMENT

CROSS REFERENCE

This application claims priority to U.S. patent application Ser. No. 13/604,369, filed Sep. 5, 2012, the specification(s) of which is/are incorporated herein in their entirety by reference.

FIELD OF THE INVENTION

The present invention related to en anti-rotation instrument which could be applied used in all health professions such as medical, dental, and any other specialties.

BACKGROUND OF THE INVENTION

Many medical or dental handles have an instrument tip, such as dental probe tip, soldered to the handle. With this design, the surgeon will have to buy a whole new instrument if his instrument tip is broken or worn out. Some medical or dental handles have the instrument tip screwed into the handle. With this design, the tip could unscrew itself from the handle during surgery which could pose a potential safety issue such as when the surgeon uses this intra-oral mirror to retract patients' tongue during surgical procedure. If the mirror head become loosened, the tongue could slip and got cut. Hence, there is a need for a medical or dental handle with a replaceable tip and with anti-rotation function during usage.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features an anti-rotation instrument system which could be used in health professions such as medical, dental, and other specialties. The device includes a main handle, a removable hand grip and an instrumental tip. The removable hand grip is attached to a female screw cavity located on the main handle. One end of the instrumental tip passes through a channel located within the hand grip while an anti-rotation key located on the instrumental tip securely resides within a dent located on the distal end of the removable hand grip. The threading located on the end of the instrumental tip is subsequently screwed into the female screw cavity of the main handle such that the hand grip is tightly sandwiched between the instrumental tip and main body.

BRIEF DESCRIPTION OF THE DRAWINGS

FIG. 13 shows a sixth alternative embodiment of a main body, a first removable hand grip, and a first instrumental tip. In some embodiments, the removable hand grip can be ergonomically shaped.

FIG. 14 shows a seventh alternative embodiment of a main body, a first removable hand grip, and a first instrumental tip.

FIG. 15 shows a sixth alternative embodiment of the instrumental tip.

DESCRIPTION OF PREFERRED EMBODIMENTS

Figure 1:
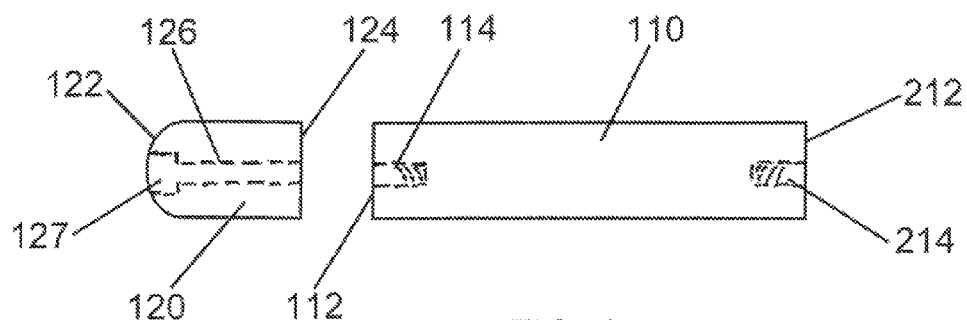
FIG. 1 shows a main body and a first removable hand grip.
Figure 2:
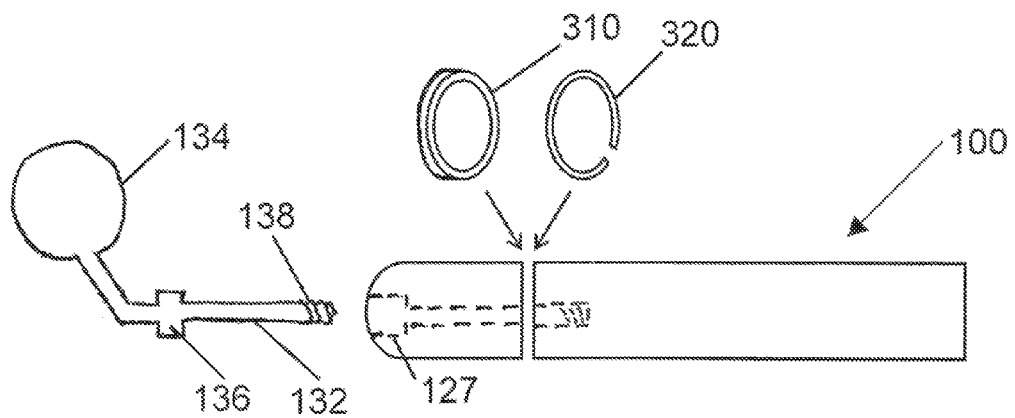
FIG. 2 shows a main body, a first removable hand grip and a first instrumental tip.
Figure 3:
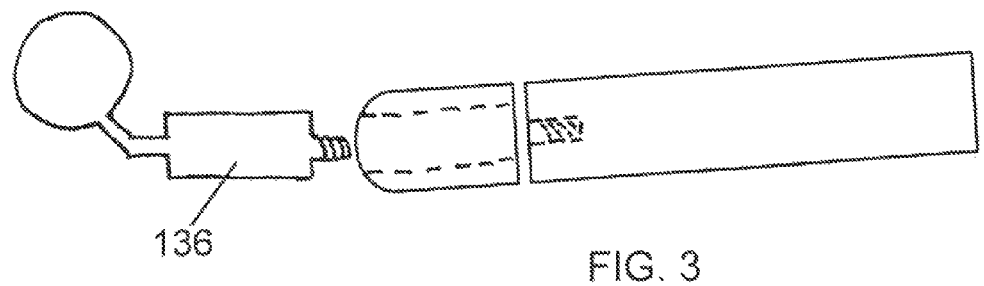
FIG. 3 shows an alternative embodiment of a main body, a first removable hand grip and a first instrumental tip.
Figure 4:
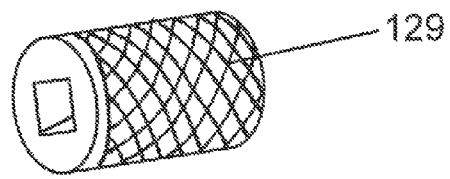
FIG. 4 shows a grip layer disposed on the removable hand grip.
Figure 5:
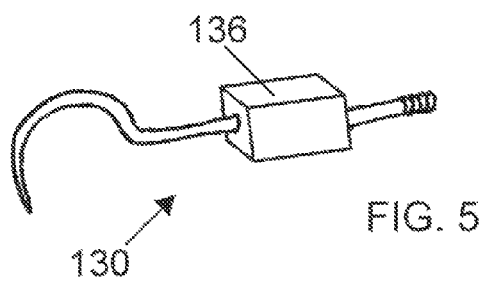
FIG. 5 shows an alternative embodiment of the instrumental tip.
Figure 6:
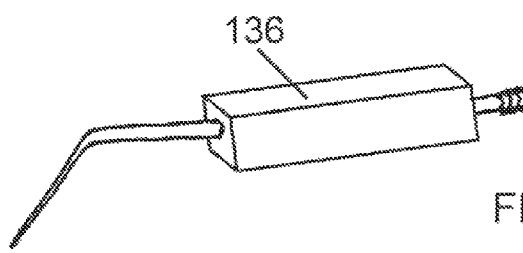
FIG. 6 shows a third alternative embodiment of the instrumental tip.

Following is a list of elements corresponding to a particular element referred to herein:

100 Anti-rotation instrument device
110 Main handle (body)
112 Handle first end
114 First female screw cavity
116 First bulge
120 First removable hand grip
122 First hand grip distal end
124 First hand grip proximal end
126 First channel
127 First dent
128 Second dent
129 Grip layer
130 First instrumental tip
132 First instrumental tip second end
134 First instrumental tip first end
136 First anti-rotation key
137 Anti-rotation key length
138 First threading
212 Handle second end
214 Second female screw cavity
216 Second bulge
220 Second removable hand grip
222 Second hand grip distal end
224 Second hand grip proximal end
226 Second channel
227 Third dent
228 Fourth dent
230 Second instrumental tip
232 Second instrumental tip second end
234 Second instrumental tip first end
236 Second anti-rotation key 238 Second threading
310 Washer
320 Spring washer Referring now to FIG. 1-15, the present invention features an anti-rotation instrument system (100). In some embodiments, the system (100) comprises a main handle (110). In some embodiments, the main handle (110) has a handle first end (112) and a handle second end (212). In some embodiments, a first female screw cavity (114) is located on the handle first end (112).

In some embodiments, the system (100) features a first removable hand grip (120). In some embodiments, the hand grip (120) has a distal end (122) and a proximal end (124). In some embodiments, a channel (126) is located through the hand grip (120) extending from the distal end (122) to the proximal end (124). In some embodiments, a first dent (127) is located on the distal end (122) of the first removable hand grip (120). In some embodiments, at least a portion of the channel (126) comprises a region having the first dent (127). In some embodiments, the first dent (127) is located on all sides of the channel (126) throughout a portion of the channel (126).

In some embodiments, the first dent (127) is located in the channel (126). In some embodiments, the first dent (127) is located on a side wall of the channel (126), for example, but not limited to the side wall of the channel (126). In some embodiments, the first dent (127) is located away from the channel (126), for example, but not limited to a terminating end of the distal end (122). In some embodiments, the first dent (127) is concentrically or centrally located on the distal end (122) of the first removable hand grip (120). In some embodiments, the first dent (127) is eccentrically located on the distal end (122) of the first removable hand grip (120).

Figure 11:
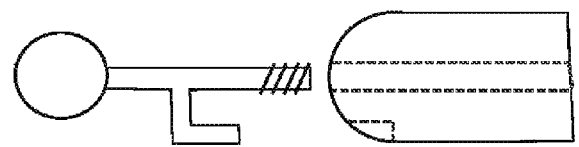
FIG. 11 shows an alternate embodiment of an anti-rotation key.
Figure 12:
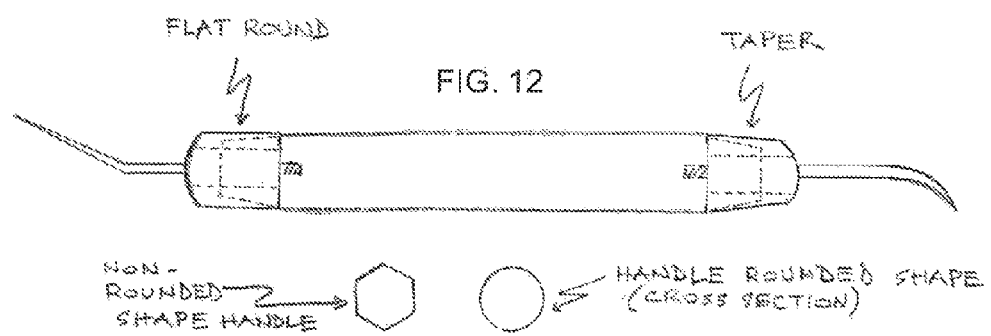
FIG. 12 shows a fifth alternative embodiment of a main body, a first removable hand grip, a first instrumental tip, a second removable hand grip and a second instrumental tip. In some embodiments, the main body can be of non-round cross-section or round shape cross-section. In some embodiments, the removable hand grip can be cylindrical or tapered shape.

In some embodiments, the system (100) features a first instrumental tip (130) having a first end (134) and a second end (132). In some embodiments, the second end (132) has a threading (138) located thereon. In some embodiments, the threading (138) matches the female screw cavity (114). In some embodiments, a first anti-rotation key (136) is located on the first instrumental tip (130). In some embodiments, the first anti-rotation key (136) is located on the tip second end. In some embodiments, the first anti-rotation key (136) is located between the tip first end (134) and the tip second end. In some embodiments, the first anti-rotation key (136) is adaptive to snuggly fit the first dent (127) located on the distal end (122) of the first removable hand grip (120). In some embodiments, the first anti-rotation key (136) is concentric with respect to the first instrumental tip (130). In some embodiments, the first anti-rotation key (136) is either eccentric with respect to the first instrumental tip (130) or could be a projection that extends from one or more sides of the first instrument tip (130). In some embodiments, the first anti-rotation key (136) projects the same direction as the second end (132) of the instrumental tip (130) like a finger (FIG. 11).

In some embodiments, the second end (132) of the instrumental tip (130) passes through the channel (126) of first hand grip (120) and the first anti-rotation key (136) securely resides within the first dent (127) located on the distal end (122) of the first removable hand grip (120). In some embodiments, the threading (138) is subsequently screwed into the first female screw cavity (114) of the main handle (110) such that the first hand grip (120) is tightly sandwiched between the first instrumental tip (130) and main body (110).

In some embodiments, the present invention features an anti-rotation instrument system which could be used in all health professions such as medical, dental, and other specialties. The system includes an anti-rotation instrument device (100) comprising a main handle (110), a first removable hand grip (120), and a first instrumental tip (130). The first removable hand grip (120) is attached to a first female screw cavity (114) located on the main handle. One end of the instrumental tip passes through a channel (126) located within first hand grip (120) with an anti-rotation key (136) located on the instrumental tip securely residing within the first dent (127) located on the distal end of the first removable hand grip (120) and the threading (138) subsequently screwed into the first female screw cavity (114) of the main handle (110) such that the First hand grip (120) is tightly sandwiched between the first instrumental tip (130) and main body (110).

The anti-rotation instrument device (100) comprises a main handle (110), a first removable hand grip (120), and a first instrumental tip (130). The main handle has a first end (112) and a second end (212), with a first female screw cavity (114) located on the first end. The removable hand grip (120) has a distal end (122) and a proximal end (124). A channel (126) is located through the hand grip extending from the distal end to the proximal end. In some embodiments, a first dent (127) is located on the distal end of the first removable hand grip and extend at least a portion of the channel (126). The first instrumental tip (130) has a first end (134) and a second end (132). In some embodiments, the second end (132) has a threading (138) located at the second end. In some embodiments, the threading (138) matches said female screw cavity (114). In some embodiments, a first anti-rotation key (136) is located on the first instrumental tip between the first end (134) and second end (132). In some embodiments, the first anti-rotation key (136) is adaptive to snuggly fit the first dent (127) located on the distal end of the first removable hand grip.

The second end (132) of the instrumental tip (130) passes through the channel (126) of first hand grip (120) with the first anti-rotation key (136) securely residing within the first dent (127) located on the distal end of the first removable hand grip (120) and the threading (138) subsequently screwed into the first female screw cavity (114) of the main handle (110) such that the first hand grip (120) is tightly sandwiched between the first instrumental tip (130) and main body (110).

In some embodiments, the system further comprises a washer (310) or a spring washer (320). In some embodiments, the washer (310) or spring washer (320) is located between the main body and the removable handgrip (120). In some embodiments, the washer (310) is made of rubber or stainless steel. In some embodiments, the second end (132) of the instrumental tip (130) is made from surgical grade stainless steel or fiberglass or acrylic, or a combination thereof.

In some embodiments, the first end (134) of the first instrumental tip (130) is any dental/medical instrument tip, for example, a mirror or a dental sickle probe or a periodontal probe. The anti-rotation key (136) is any non-rotatable key, such as for example, flat key, rectangle key, hex key, square key or oval key. In some embodiments, the anti-rotation key (136) is any non-round key that allows for catching or fixing within the dent to prevent spinning of the key or the instrumental tip.

In some embodiments, the first dent (127) extends throughout of the channel (126) of the first removable hand grip (120). In some embodiments, the first anti-rotation key (136) has a length (137) equal to the length of the channel (130).

In some embodiments, the main body (110) has a cylindrical shape and the first removable hand grip (120) has also a cylindrical shape. In some embodiments, the first removable hand grip (120) has a grip layer (129) located on exterior surface. In some embodiments, the grip (129) has a dot or line, pattern located on grip surface for grip enhancement. In some embodiments, the grip (129) may be round with a rough surface for gripping. In some embodiments, the grip (129) may be an irregular shape (or non-round shape) with or without a rough surface. In some embodiments, the grip layer (129) is made from stainless steel or rubber. In some embodiments, the grip pattern is done by embossing during hand grip manufacturing.

In some embodiments, the system further comprises a first bulge (116) located on the first end (112) of the main body (110) and a second dent located on the proximal end of the first removable grip (120). The first female screw cavity (114) passes through the first bulge (116) and the second dent (128) is adaptive to snuggly fit the first bulge (116).

The second end (132) of the instrumental tip (130) passes through the channel (126) of first hand grip (120) with the first anti-rotation key (136) securely reside within the first dent (127) located on the distal end of the first removable hand grip (120) and wherein the threading (138) is subsequently screwed into the first female screw cavity (114) of the main handle (110) such that the first bulge (116) is snuggly fitted into the second dent (128) of the first removable grip (120) and such that the first hand grip (120) is tightly sandwiched between the first instrumental tip (130) and main body (110).

Figure 7:
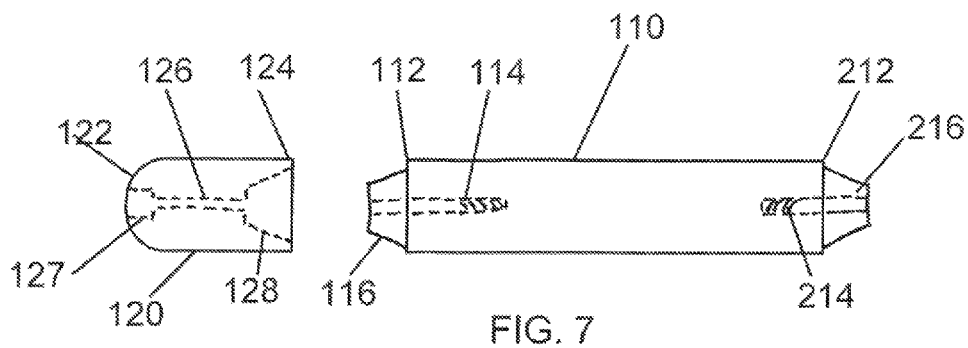
FIG. 7 shows a third alternative embodiment of a main body, a first removable hand grip and a first instrumental tip.
Figure 8:
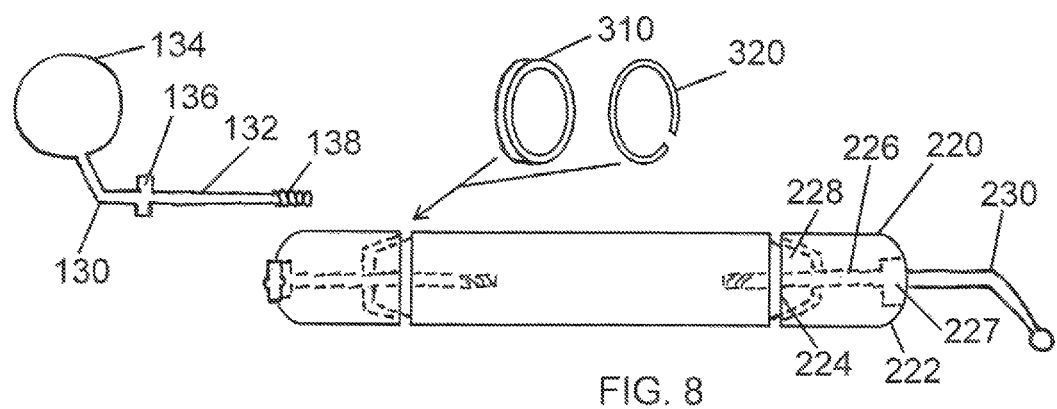
FIG. 8 shows a fourth alternative embodiment of a main body, a first removable hand grip, a first instrumental tip, a second removable hand grip and a second instrumental tip.
Figure 9:
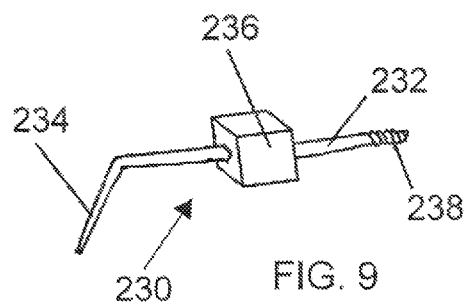
FIG. 9 shows a fourth alternative embodiment of the instrumental tip.
Figure 10:
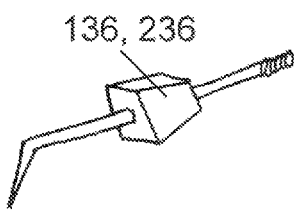
FIG. 10 shows a fifth alternative embodiment of the instrumental tip. In some embodiments, an anti-rotation key is a trapezoidal prism.

In some embodiments, the second end (212) of the main body (110) has similar configuration as the first end (112) with a female screw cavity for the attachment of a second hand grip and a second instrumental tip. The second tip can be the same or different from the first instrumental tip, as shown in FIGS. 7-8.

In some embodiments, the anti-rotation instrument device (100) further comprises of a second bulge (216) located on the second end (212) of the main body (110), a second removable hand grip (220), a second instrumental tip (230). A second female screw cavity (214) is located on the second end. The second removable hand grip (220) has a distal end (222) and proximal end (224). In some embodiments, a second channel (226) is located through the hand grip extending from the distal end to the proximal end. In some embodiments, a third dent (227) is located on the proximal end of the second removable grip and extends at least a portion of the second channel (226). A fourth dent (228) is located on the distal end of the first removable hand grip and is adaptive to snuggly fit second bulge (216).

The second instrumental tip (230) has a second end tip (234) and a second end (232). In some embodiments, the second end (232) has a second threading (238) located at the second end. In some embodiments, the threading (238) matches the second female screw cavity (214). In some embodiments, a second anti-rotation key (236) is located on the second instrumental tip between the first end (234) and second end (232). In some embodiments, the second anti-rotation key (236) is adaptive to snuggly fit the third dent (227) located on the distal end of the second removable hand grip and wherein the second threading (238) is subsequently screwed into the second female screw cavity (214) of the main handle (110) such that the second hand grip (220) is tightly sandwiched between the second instrumental tip (230) and main body (110).

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An anti-rotation instrument system for medical and dental applications, the system comprising an anti-rotation instrument device (100) comprising:
   (a) a main handle (110), wherein the main handle has a handle first end (112) and a handle second end (212), wherein a first female screw cavity (114) is disposed on the handle first end (112), wherein a second female screw cavity (214) is located on the handle second end (212);
   (b) a first removable hand grip (120), wherein the removable hand grip has a distal end (122) and a proximal end (124), wherein a channel (126) is disposed through the hand grip extending from the distal end to the proximal end, wherein a first dent (127) is disposed on the distal end of the first removable hand grip and extends at least a portion of the channel (126), wherein the first dent (127) is a non-round dent; and
   (c) a first instrumental tip (130) having a first end (134) and a second end (132), wherein the second end (132) has a threading (138) disposed at the second end, wherein the threading (138) matches said female screw cavity (114), wherein a first anti-rotation key (136) is disposed on the first instrumental tip between the first end (134) and second end (132), wherein the anti-rotation key (136) is a non-round key, wherein the anti-rotation key (136) is a flat key, a rectangle key, a hex key, a square key or an oval key, wherein the first anti-rotation key (136) is adaptive to snuggly fit the first dent (127) disposed on the distal end of the first removable hand grip;
   (d) a first bulge (116) disposed on the first end (112) of the main body (110), wherein the first female screw cavity (114) passes through the first bulge;
   (e) a second dent (128) disposed on the proximal end of the first removable grip (120), wherein the second dent (128) is adaptive to snuggly fit the first bulge (116), wherein the second end (132) of the instrumental tip (130) passes through the channel (126) of first hand grip (120) with the first anti-rotation key (136) securely resides within the first dent (127) disposed on the distal end of the first removable hand grip (120) and wherein the threading (138) is subsequently screwed into the first female screw cavity (114) of the main handle (110) such that the first bulge (116) is snuggly fit into the second dent of the first removable grip (120) and such that the first hand grip (120) is tightly sandwiched between the first instrumental tip (130) and main body (110);

(f) a second bulge (216) disposed on the second end (212) of the main body (110);

(g) a second removable hand grip (220), wherein the second removable hand grip (220) has a distal end (222) and a proximal end (224), wherein a second channel (226) is located through the hand grip extending from the distal end to the proximal end, wherein a third dent (227) is located on the distal end of the second removable grip and extends at least a portion of the second channel (226), and wherein a fourth dent (228) is located on the proximal end of the second removable hand grip and is adapt to snuggly fit the second bulge (216); and (h) a second instrumental tip (230), wherein the second instrumental tip (230) has a second end tip (234) and a second end (232), wherein the second end (232) has a second threading (238) located at the second end, wherein the threading (238) matches the second female screw cavity (214), wherein a second anti-rotation key (236) is located on the second instrumental tip between the second end tip (234) and second end (232), wherein the second anti-rotation key (236) is adaptive to snuggly fit the third dent (227) located on the proximal end of the second removable hand grip and wherein the second threading (238) is subsequently screwed into the second female screw cavity (214) of the main handle (110) such that the second bulge (216) is snuggly fit into the fourth dent (228) of the second removable grip (220) and such that the second hand grip (220) is tightly sandwiched between the second instrument tip (230) and main body (110).

2. The instrument system of claim 1, wherein the system further comprises a washer (310) or a spring washer (320), wherein the washer (310) or spring washer (320) are disposed between the main body (110) and the hand grips (120, 220).

3. The instrument system of claim 2, wherein the washer (310) is made of rubber or stainless steel.

4. The instrument system of claim 1, wherein the first end (134) and/or second end (132) of the instrumental tip (130) is made from surgical grade stainless steel or fiberglass or acrylic, or a combination thereof.

5. The instrument system of claim 1, wherein the first end (134) of the first instrumental tip (130) is a mirror, a dental sickle probe, a periodontal probe, or a surgical blade.

6. The instrument system of claim 1, wherein the main body (110) has a cylindrical shape or non-round shape.

7. An anti-rotation instrument system for medical and dental applications, the system comprising an anti-rotation instrument device (100) comprising:

(a) a main handle (110), wherein the main handle has a handle first end (112) and a handle second end (212), wherein a first female screw cavity (114) is disposed on the handle first end (112), wherein a second female screw cavity (214) is located on the handle second end (212);

(b) a first removable hand grip (120), wherein the removable hand grip has a distal end (122) and a proximal end (124), wherein a channel (126) is disposed through the hand grip extending from the distal end to the proximal end, wherein a first dent (127) is disposed on the distal end of the first removable hand grip and extends at least a portion of the channel (126), wherein the first dent (127) is a non-round dent; and (c) a first instrumental tip (130) having a first end (134) and a second end (132), wherein the second end (132) has a threading (138) disposed at the second end, wherein the threading (138) matches said female screw cavity (114), wherein a first anti-rotation key (136) is disposed on the first instrumental tip between the first end (134) and second end (132), wherein the anti-rotation key (136) is a non-round key, wherein the anti-rotation key (136) is a flat key, a rectangle key, a hex key, a square key or an oval key, wherein the first anti-rotation key (136) is adaptive to snuggly fit the first dent (127) disposed on the distal end of the first removable hand grip;

(d) a first bulge (116) disposed on the first end (112) of the main body (110), wherein the first female screw cavity (114) passes through the first bulge;

(e) a second dent (128) disposed on the proximal end of the first removable grip (120), wherein the second dent (128) is adaptive to snuggly fit the first bulge (116), wherein the second end (132) of the instrumental tip (130) passes through the channel (126) of first hand grip (120) with the first anti-rotation key (136) securely resides within the first dent (127) disposed on the distal end of the first removable hand grip (120) and wherein the threading (138) is subsequently screwed into the first female screw cavity (114) of the main handle (110) such that the first bulge (116) is snuggly fit into the second dent of the first removable grip (120) and such that the first hand grip (120) is tightly sandwiched between the first instrumental tip (130) and main body (110);

(f) a second bulge (216) disposed on the second end (212) of the main body (110);

(g) a second removable hand grip (220), wherein the second removable hand grip (220) has a distal end (222) and a proximal end (224), wherein a second channel (226) is located through the hand grip extending from the distal end to the proximal end, wherein a third dent (227) is located on the distal end of the second removable grip and extends at least a portion of the second channel (226), and wherein a fourth dent (228) is located on the proximal end of the second removable hand grip and is adapt to snuggly fit the second bulge (216); and (h) a second instrumental tip (230), wherein the second instrumental tip (230) has a second end tip (234) and a second end (232), wherein the second end (232) has a second threading (238) located at the second end, wherein the threading (238) matches the second female screw cavity (214), wherein a second anti-rotation key (236) is located on the second instrumental tip between the second end tip (234) and second end (232), wherein the second anti-rotation key (236) is adaptive to snuggly fit the third dent (227) located on the proximal end of the second removable hand grip and wherein the second threading (238) is subsequently screwed into the second female screw cavity (214) of the main handle (110) such that the second bulge (216) is snuggly fit into the fourth dent (228) of the second removable grip (220) and such that the second hand grip (220)

is tightly sandwiched between the second instrument tip (230) and main body (110) wherein the first removable hand grip (120) has a grip layer (129) disposed on exterior surface.

8. The instrument system of claim 7, wherein the grip (129) has a dot or line, pattern.

9. The instrument system of claim 7, wherein the grip layer (129) is made from stainless steel or rubber.

* * * * *